United States Patent
Han

(10) Patent No.: US 11,439,487 B2
(45) Date of Patent: Sep. 13, 2022

(54) SYSTEMS AND METHODS FOR AN EVACUATOR ADAPTER

(71) Applicant: Edison Sangwoo Han, Fullerton, CA (US)

(72) Inventor: Edison Sangwoo Han, Fullerton, CA (US)

(*) Notice: Subject to any disclaimer, the term of this patent is extended or adjusted under 35 U.S.C. 154(b) by 0 days.

(21) Appl. No.: 17/366,956

(22) Filed: Jul. 2, 2021

(65) Prior Publication Data

US 2022/0000595 A1 Jan. 6, 2022

Related U.S. Application Data

(60) Provisional application No. 63/048,024, filed on Jul. 3, 2020.

(51) Int. Cl.
*A61M 1/00* (2006.01)
*A61C 17/08* (2006.01)

(52) U.S. Cl.
CPC ............. *A61C 17/08* (2019.05); *A61M 1/79* (2021.05); *A61M 1/804* (2021.05); *A61M 2205/103* (2013.01); *A61M 2206/20* (2013.01)

(58) Field of Classification Search
CPC ..... A61M 1/08; A61M 1/0003; A61H 9/0021; A61H 9/0028; A61H 9/005; A61H 9/0057; A61H 2009/0064; A61H 9/0071
See application file for complete search history.

(56) References Cited

U.S. PATENT DOCUMENTS

| | | | | |
|---|---|---|---|---|
| 1,238,061 A | * | 8/1917 | Bourdelat | B26B 19/44 30/43.2 |
| 1,882,040 A | * | 10/1932 | Roehm | A61H 9/005 601/6 |
| 1,983,601 A | * | 12/1934 | Conn | A61B 17/24 604/22 |
| 2,338,339 A | * | 1/1944 | La Mere | A61H 23/04 601/7 |
| 4,970,787 A | * | 11/1990 | Watanabe | B26B 19/44 30/41.5 |

(Continued)

FOREIGN PATENT DOCUMENTS

CN 208799463 U 4/2019
WO 2020040651 A1 2/2020

OTHER PUBLICATIONS

Dr. David G. Charlton, DDS, Journal of Military Medicine, "Determination of Minimum Suction Level Necessary for Field Dental Units," vol. 175, Apr. 2010.

(Continued)

*Primary Examiner* — Adam Marcetich
(74) *Attorney, Agent, or Firm* — Concept IP LLP; Pejman Yedidsion

(57) ABSTRACT

An adapter for an evacuator for increasing a suction power of the evacuator includes a suction assembly adapted to be coupled with the evacuator. The suction assembly has a housing, an impeller arranged inside the housing and configured to provide a suction, and an inlet conduit to facilitate a flow of fluid to the impeller. The suction assembly also includes an outlet conduit arranged inside the housing and adapted to be coupled to the evacuator. The outlet conduit is in fluid communication with the impeller and facilitates a flow of the fluid from the suction assembly to the evacuator.

20 Claims, 17 Drawing Sheets

(56) References Cited

U.S. PATENT DOCUMENTS

| | | | | |
|---|---|---|---|---|
| 5,295,956 A * | 3/1994 | Bales | | A61M 1/7415 604/30 |
| 6,086,587 A * | 7/2000 | Hawk | | A61B 17/88 606/53 |
| 6,159,226 A * | 12/2000 | Kim | | A61B 17/244 606/161 |
| 6,196,982 B1 * | 3/2001 | Ball | | A61H 9/0057 601/12 |
| 10,285,543 B1 * | 5/2019 | Hall | | A47K 3/281 |
| 2002/0173744 A1 | 11/2002 | Epstein | | |
| 2002/0198488 A1 * | 12/2002 | Yao | | A61M 1/0062 604/35 |
| 2003/0097142 A1 * | 5/2003 | Wang | | A61M 1/0023 606/162 |
| 2003/0106183 A1 * | 6/2003 | Frederick | | A47L 9/0416 15/387 |
| 2003/0109854 A1 * | 6/2003 | Chen | | A61M 1/0023 604/540 |
| 2005/0075600 A1 | 4/2005 | Nelson et al. | | |
| 2007/0156124 A1 * | 7/2007 | Ignon | | A61M 1/962 606/9 |
| 2008/0208112 A1 * | 8/2008 | Bensoussan | | A61M 1/0003 604/35 |
| 2009/0048581 A1 * | 2/2009 | Sebban | | A61M 1/0003 604/540 |
| 2012/0005821 A1 * | 1/2012 | Fowkes | | A47K 3/002 4/581 |
| 2013/0326805 A1 * | 12/2013 | Skrzyniarz | | A47K 3/127 4/572.1 |
| 2014/0130247 A1 * | 5/2014 | Marshall | | A47K 3/125 4/573.1 |
| 2014/0140815 A1 * | 5/2014 | Shener-Irmakoglu | | A61B 17/32002 417/478 |
| 2014/0375434 A1 * | 12/2014 | Puljan | | F21V 33/004 340/12.5 |
| 2015/0051620 A1 * | 2/2015 | Presser | | A61B 17/54 606/131 |
| 2015/0314050 A1 * | 11/2015 | Beer | | A61M 1/0023 604/267 |
| 2016/0271305 A1 * | 9/2016 | Kurihara | | A61M 1/0011 |
| 2017/0319759 A1 * | 11/2017 | Ahluwalia | | A61M 1/743 |
| 2018/0185063 A1 * | 7/2018 | DiMitri | | A47K 7/026 |
| 2019/0175202 A1 * | 6/2019 | Piatyszek | | A61B 17/24 |
| 2021/0030931 A1 * | 2/2021 | Sant | | A61M 3/0279 |

OTHER PUBLICATIONS

International Search Report and Written Opinion for PCT/US21/40327, dated Oct. 20, 2021.

* cited by examiner

SYSTEMS AND METHODS FOR AN EVACUATOR ADAPTER

CROSS-REFERENCE TO RELATED APPLICATIONS

This application claims priority to and the benefit of U.S. Provisional Patent Application No. 63/048,024, filed Jul. 3, 2020, the contents of which are hereby incorporated by reference herein for all purposes.

TECHNICAL FIELD

Embodiments relate generally to dental tools, and more particularly to high-volume and low-volume evacuators.

BACKGROUND

Critical infection prevention and control functions have become significantly more important during the medical and dental procedures that may impose a higher risk for health care personnel and patients. According to the Centers for Diseases Control and Prevention (CDC), "SARS-CoV-2", the virus that causes COVID-19, is thought to be spread primarily through respiratory droplets when an infected person coughs, sneezes, or talks. The virus has been shown to persist in aerosols for hours and on some surfaces for days under laboratory conditions. COVID-19 may be spread by people who are not showing symptoms.

The practice of dentistry involves the use of rotary dental and surgical instruments, such as hand-pieces or ultrasonic scalers and air-water syringes. These instruments create a visible spray or aerosol that can contain particle droplets of water, saliva, blood, microorganisms, and other debris. Aerosol can stay in the air for many hours.

Surgical masks protect mucous membranes of the mouth and nose from droplet spatter, but surgical masks do not provide complete protection against inhalation of airborne infectious agents. As the more infectious variant COVID-19 viruses are emerging, the need to capture aerosol and/or fluids generated during dental and medical procedures has become absolutely necessary.

SUMMARY

A system embodiment may include an adapter for an evacuator for increasing a suction power of the evacuator. The adapter includes a suction assembly adapted to be coupled with the evacuator. The suction assembly has a housing, an impeller arranged inside the housing and configured to provide a suction, and an inlet conduit to facilitate a flow from a mouth of a patient to the impeller. The suction assembly also includes an outlet conduit arranged inside the housing and adapted to be coupled to the evacuator. The outlet conduit is in fluid communication with the impeller and facilitates a flow of the fluid from the suction assembly to the evacuator.

In an embodiment, the adapter further includes a tube removably coupled to the inlet conduit and arranged outside the housing. The tube is a venturi tube and tapers outwardly from the inlet conduit in a direction away from the inlet conduit. In one embodiment, the adapter further includes a tip structure coupled to the tube to enable a suction of fluid from the inside of the mouth of the patient. In an embodiment, the adapter includes three types of tubes, for example, the venturi tube, a triple helix tube, and a shark fin tube.

In one embodiment, the adapter further includes a mesh arranged at an interface of the tip structure and the tube to protect the impeller from solid objects. In one embodiment, the adapter further includes an impeller mechanism disposed inside the tube and arranged along an inner wall of the tube to create a vortex inside the tube and disintegrate particles flowing through the tube.

In one embodiment, the impeller mechanism includes a plurality of fins arranged in a plurality of rows inside the tube, where each row extends spirally from a first end section of the tube to a second end section of the tube. In one embodiment, the fins arranged at a cross-section of the tube are arranged at a predefined angular orientation from the fins arranged at an adjacent cross-section. In one embodiment, each fin includes a shark fin shape. The tube having the plurality of fins is referred to as the shark fin tube.

In one embodiment, the impeller mechanism includes a plurality of helical strands extending from a front end section of the tube to a rear-end section of the tube. The strands are arranged at a fixed predetermined angle relative to each other throughout the extension of the strands inside the tube. In one embodiment, each of the plurality of strands includes a sharp edge to facilitate a breaking of the particles present inside the fluid. The tube having three helical strands is referred to as the triple helix tube. In one embodiment, the tube is a hollow venturi tube and devoid of any type of impeller mechanism.

In one embodiment, the adapter further includes a suction connector adapted to engage with the inlet conduit to facilitate a capture of aerosols and spatters coming outside the mouth of the patient. The suction connector includes a conduit portion adapted to engage with the inlet conduit and a collector portion to collect the aerosol generated during the procedures and extending outwardly and away from the conduit portion. In one embodiment, the collector portion includes a funnel portion engaged with the conduit portion and a cover portion adapted to removably engage with the funnel portion and defining a cavity therebetween. The cover portion defines a plurality of openings to capture the aerosols and spatters coming outside the mouth of the patient.

In one embodiment, the cover portion includes a plug removably coupled to a central conduit of the cover portion to close an inlet port of the central conduit. The central conduit is adapted to connect to a evacuator tip to facilitate an extraction of the fluid from inside the mouth. In one embodiment, the cover portion includes a plurality of guide conduits extending inside the cavity and along a rear surface of the cover portion. The guide conduits are in fluid communication with the plurality of openings to enable a flow of the fluid entering the plurality of openings to the conduit portion.

In one embodiment, the cover portion includes a concave shape having a front concave surface. The openings are defined at the front concave surface. In one embodiment, the collector portion includes a shape of a shower pad. In one embodiment, the suction assembly further includes a trigger switch to control a suction power of the adapter. In one embodiment, the trigger switch controls a rotational speed of the impeller to control the suction power of the adapter.

In one embodiment, the housing includes a hand-gun shape having a barrel portion and a handle, where the inlet conduit is arranged inside the barrel portion, and the outlet conduit extends inside the handle. In one embodiment, the outlet conduit tapers inwardly from the impeller in a direction away from the impeller along a length of the handle. In one embodiment, the handle extends downwardly of the barrel portion and is arranged at an angle greater than or equal to 90 degrees relative to the barrel portion.

BRIEF DESCRIPTION OF THE DRAWINGS

The components in the figures are not necessarily to scale, emphasis instead being placed upon illustrating the principals of the invention. Like reference numerals designate corresponding parts throughout the different views. Embodiments are illustrated by way of example and not limitation in the figures of the accompanying drawings, in which.

DETAILED DESCRIPTION

Figure 1:
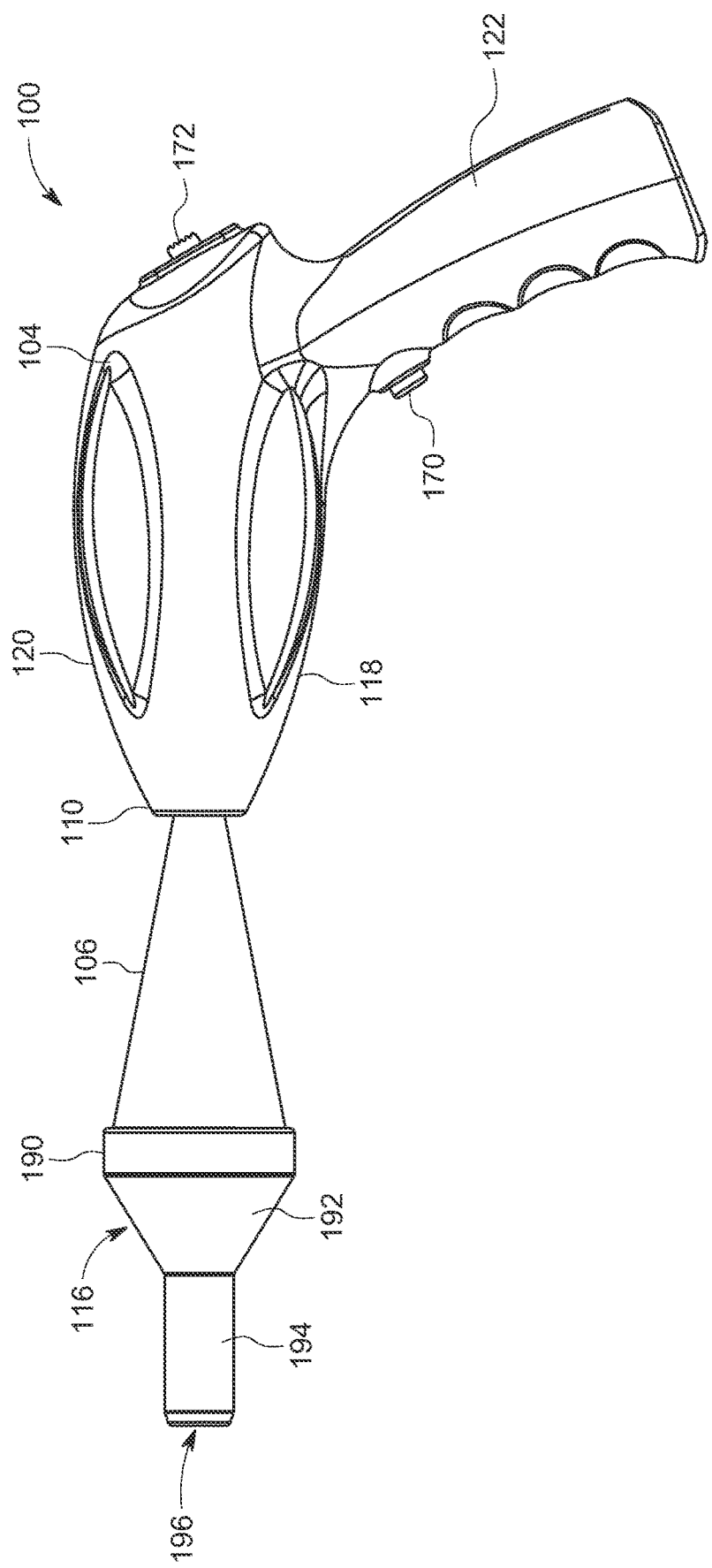
FIG. 1 depicts a side view of an adapter suitable for attachment to an evacuator, according to an embodiment of the disclosure.

The presently disclosed systems, devices, and methods allow for an adapter for an evacuator, such as a high-volume evacuator (HVE) or a low-volume evacuator (LVE) that increases the suction power of the evacuator. In one embodiment, the adapter enables an airflow rate of approx. 4.5 SCFM or more when the adapter is connected to HVE. According to the Journal of Military Medicine, "Determination of Minimum Suction Level Necessary for Field Dental Units," (Vol 175, April 2010), published by Dr. David G. Charlton, DDS, "evaluators determined that airflow rate of 4.5 SCFM and greater resulted in suction levels they judged to be clinically adequate" for routine dental procedures. The adapter may be a portable adapter in one embodiment and may be a hand-held adapter to be held by a dental assistant. In some embodiments, the adapter may be mounted, such as to a dental chair. In one embodiment, as shown in FIG. 1, the adapter 100 may have a hand-gun shape with a handle for an operator, such as a dental assistant, to hold the adapter 100. The ergonomic shape may help reduce hand fatigue. The hand-gun shape with a handle at approximately 90 degrees to a barrel portion may be configured to prevent a reversal of fluid or aerosol flow into the mouth. Thus, there is no need for one way valve. In one embodiment, the adapter 100 is made of plastic.

The American Dental Association (ADA) recommends dentists "employ the lowest aerosol-generating armamentarium when delivering any type of dental care." The ADA recommends dentists utilize rubber dams or hands-free suction and retraction-like systems in conjunction with a high-volume evacuator (HVE) to reduce spatter. According to a study published in the Journal of the American Dental Association, using a suction and retraction-like system, such as an ISOLITE™ system, can help protect the health of dental clinicians by releasing significantly less spatter into the environment than using an HVE alone. Most intraoral retraction-like systems are also known as spatter reduction devices (e.g., intraoral suction system) and must be connected to one of the HVE tubes. ADA recommends using an intraoral suction system in conjunction with an HVE device. When performing any dental procedure, including surgery, an assistant must need to use an HVE device in addition to the intraoral suction device. However, when both devices are in use, the vacuum power decreases significantly as both devices are connected to a single PVC pipe. Hence, vacuum power may decrease by approximately 40-50% when both the HVE device and the intraoral suction device are turned on simultaneously.

Additionally, a dental delivery unit is attached to a dental chair and has two HVE tubes (½ inch in diameter) and one LVE tube (3/16 inch in diameter). These tubes have specific connectors that allow them to fit disposable tips or retraction-like systems. These tubes are attached to a single PVC pipe (range from ¾ inch diameter to 1½ inch) that is connected to the main PVC pipe (usually 1½ to 2 inches in diameter) that extends from the main vacuum pump. Most of the time, more than one dental chair delivery system may be extended out from the main PVC pipe.

Vacuum power is limited to the size of the PVC pipe (usually 1½ to 2 inches in diameter) extending from the main vacuum pump associated with the HVE. Changing the main vacuum pump to a higher horsepower may not necessarily increase the suction power. Also, the suction power can be affected by many reasons such as a low horsepower, the length and the size of the PVC pipes, configuration of PVC pipe connections from the chairs to the main vacuum, biofilms and debris accumulation inside the pipes, number of HVE and LVE being used simultaneously, etc.

Extra-oral vacuum systems may be used to suction the droplets and aerosol; however, the extra-oral filtration system may leak contaminated aerosol back out into the air. Additionally, due to the size of an extra-oral system, it is not feasible to employ an extra-oral system in small dental offices. The embodiments of the present invention can be used to restore power to the suction system if the current pump is not working at full capacity for any reason. It may also be temporarily used as an emergency suction device if the central vacuum shuts down for any reason.

Figure 2:
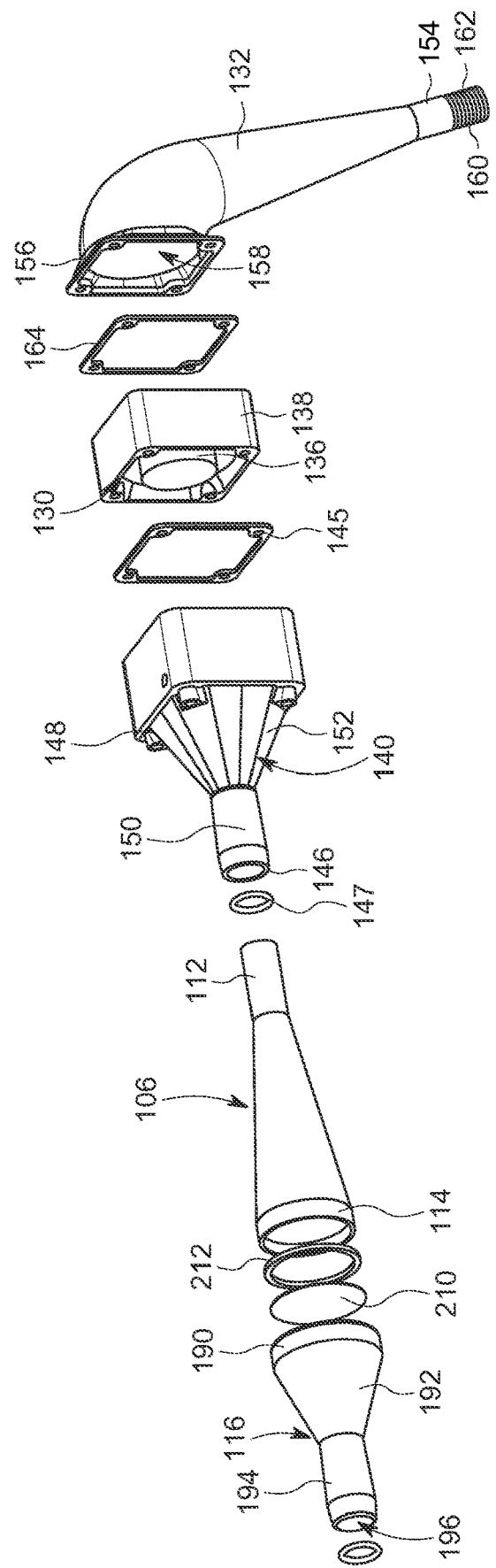
FIG. 2 depicts an exploded view of the adapter of FIG. 1 with a housing removed and showing various components of the adapter, according to an embodiment of the disclosure.

As shown in FIG. 1 and FIG. 2, the adapter 100 includes a suction assembly 104, a tube 106 removably coupled to the suction assembly 104 and arranged at a first end 110 (i.e., a front end 110) of the suction assembly 104. The tube 106 extends in a longitudinal direction and away from the front end 110 of the suction assembly 104, and includes a first end section 112 (i.e., a rear-end section 112) connected to the suction assembly 104, and a second end section 114 (i.e., the front end section 114) arranged distally from the suction assembly 104. Further, the adapter 100 includes a tip structure 116 connected to the front end section 114 of the tube 106 and extending forwardly of the front end section 114 of the tube 106. A standard HVE tip may be inserted into the tip structure 116 to enable a suction of saliva, blood, etc., from an inside of the mouth by the adapter 100.

In one embodiment, referring to FIG. 2, the tube 106 is a venturi tube, and may measure and/or increase the flow of a fluid, such as aerosols or splatter emerging from the mouth. As shown, the tube 106 is a hollow tube having a frusto-conical shape with an inner diameter decreasing from the front end section 114 to the rear-end suction 112. Accordingly, the tube 106 has a first diameter at the front end section 114 and a second diameter smaller than the first diameter at the rear end section 112. In this manner, the fluid flows at a higher velocity at the rear-end section 112 than through the front end section 114, thereby creating a pressure differential that is a measure of the flow of the fluid.

In one embodiment, the rear end section 112 may have a diameter of 10 mm, and the tube 106 may taper outwardly from the rear-end portion 112. In one embodiment, the front end section 114 may have a diameter of 40 mm, with the tube 106 tapering inwardly toward the rear end section 112. In one embodiment, the length from end section 114 to the rear end section 112 is 100 mm. The tube 106 may be detachably/removably coupled to the suction assembly 104. In an embodiment, the tube 106 may be in a threaded engagement with a housing 118 or one more component arranged inside the housing 118 of the suction assembly 104. In another embodiment, the tube 106 may be press fitted with the housing 118 or one or more components of the suction assembly and extends inside housing 118.

Figure 3:
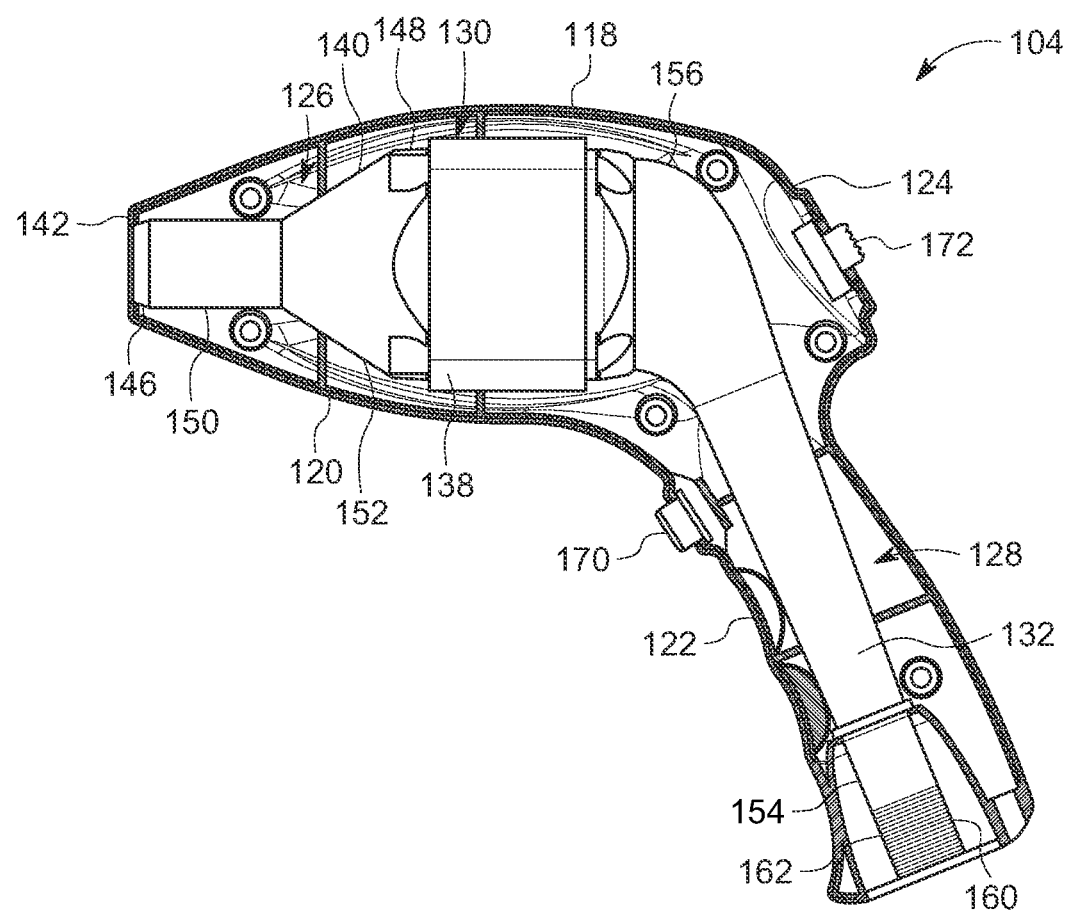
FIG. 3 depicts a suction assembly of the adapter of FIG. 1 with a half portion of the housing removed, according to an embodiment of the disclosure.

Referring to FIG. 3, the suction assembly 104 includes the housing 118 having a barrel portion 120 and a handle 122 extending downwardly from the barrel portion 120 and arranged proximate to a rear end 124 of the barrel portion 120. The handle 122 facilitates a holding of the adapter 100. The handle 122 is configured to have a set of grooves for the fingers to wrap around for the user to have a comfortable and secure grip. In one embodiment, the handle 122 extends at an obtuse angle relative to the barrel portion 120. In some embodiments, the handle 122 is arranged at approximately 90 degrees angle relative to the barrel portion 120. As shown, the barrel portion 120 defines a first chamber 126 of the housing 118, and the handle 122 defines a second chamber 128 of the housing 118. The suction assembly 104 further includes an impeller assembly 130 arranged inside the first chamber 126 and an outlet conduit 132 coupled to the impeller assembly 130 and arranged inside the second chamber 128.

Figure 4:
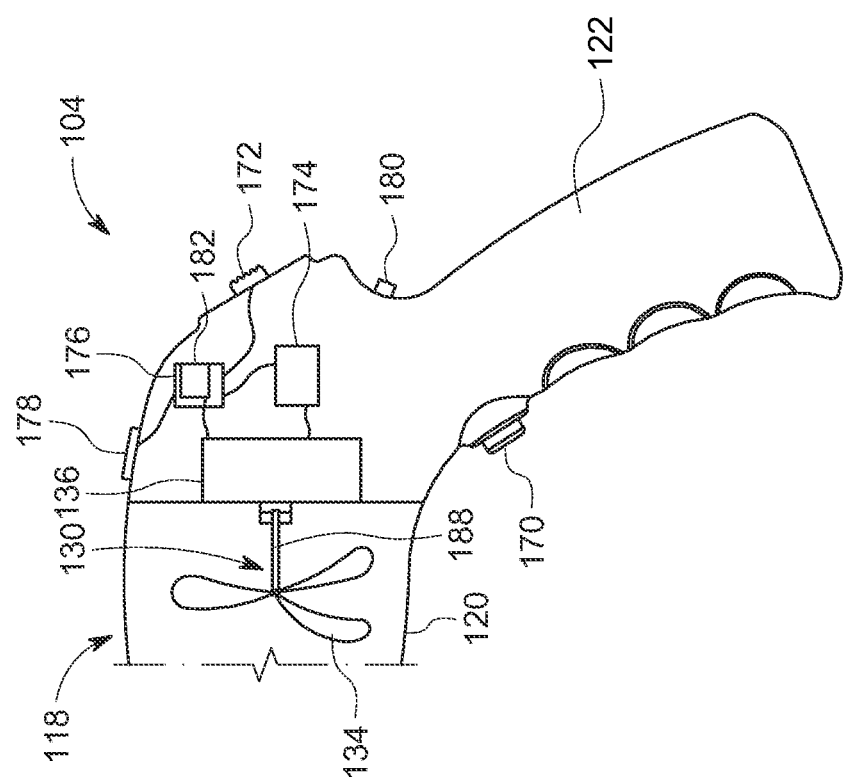
FIG. 4 depicts a schematic of a portion of the suction assembly schematically depicting various electrical components of the suction assembly, according to an embodiment of the disclosure.

In an embodiment, referring to FIGS. 2 and 4, the impeller assembly 130 includes an impeller 134 (shown in FIG. 4) and a motor 136 driving the impeller 134, and an impeller housing 138. The impeller 134 and the motor 136 may be located inside the impeller housing 138 that is fluidly connected to the tube 106. As shown in FIGS. 2 and 3, fluid exiting the tube 106 will enter an inlet conduit 140 which extends outwardly from the impeller housing 138 to a front end 142 of the housing 118. The housing 118 defines the front opening at the front end 142 through with the tube 106 extends inside the housing 118 and connects to the inlet conduit 140. The inlet conduit 140 may be connected to tube 106 by using suitable threads or may be press-fitted to the tube 106. As shown in FIGS. 2 and 3, the inlet conduit 140 includes a first end 146 adapted to be coupled to the tube 106 and a second end 148 coupled to the impeller housing 138. In an embodiment, the inlet conduit 140 is integrally formed with the impeller housing 138. In an embodiment, a gasket 145 may be disposed between the impeller housing 138 and the inlet conduit 140 to prevent any leakage of the fluid at an interface of the impeller housing 138 and the inlet conduit 140. Similarly, a sealing ring 147 may be arranged between the tube 106 and the inlet conduit 140 to prevent any leakage of fluid at the interface.

Further, the inlet conduit 140 may include a first portion 150 having a substantially constant diameter and a second portion that tapers outwardly from the first portion 150 to the second end 148. Accordingly, a diameter of the inlet conduit 140 increases from the first portion 150 towards the second end 148. In an embodiment, a screen (not shown) may be arranged inside the inlet conduit 140 and is located at an interface of the first portion 150 and the second portion 152. The screen may protect the impeller 134 from solid objects suctioned into the adapter 100. In one embodiment, the screen may be removable for cleaning or for replacement with another screen. In one embodiment, the screen is made of a thin metal material, such as copper, or alternatively stainless steel mesh or plastic material. In one embodiment, the screen may have holes sized to capture large particles and debris.

Fluids entering the inlet conduit 140 encounter the impeller 134 and flow to the outlet conduit 132. The outlet conduit 132 extends through the handle 122 of the housing 118 and has a distal end portion 154 for connection of the adapter 100 to a vacuum or evacuator, such as an HVE or LVE. In one embodiment, the impeller 134 provides for enhanced suctioning power of the adapter 100. In an embodiment, the impeller 134 and the motor 136 may generate a predefined amount of airflow, for example, 4.5 SCFM, and may be submerged in water for a prolonged time, for example, thirty minutes As shown in FIGS. 2 and 3, the outlet conduit 132 includes a first end portion 156 attached to the impeller housing 138 and tapers inwardly to the distal end portion 154. Accordingly, a size of an opening 158 of the outlet conduit 132 at the first end portion 156 is larger than a size of an opening (not shown) of the outlet conduit 132 at the distal end portion 154. In an embodiment, the opening 158 includes a rectangular shape, while the opening at the distal end portion 154 includes a substantially circular shape. Further, to facilitate a connection of the adapter 100 with an evacuator, the distal end portion 154 may include a threaded portion 160 having threads 162. In some embodiments, the outlet conduit 132 may form a friction fit with the evacuator. Further, a gasket 164 may be arranged between the outlet conduit 132 and the impeller housing 138 to prevent a leakage of fluid from a junction of the impeller housing 138 and the outlet conduit 132. As the outlet conduit 132 extends through the handle 122, the outlet conduit 132 is arranged substantially perpendicularly to the inlet conduit 140, and hence prevents a back flow of the fluid from the suction assembly 104 to the mouth of the patient.

In another embodiment, the distal end portion 154 of the outlet conduit 132 may have a slightly smaller diameter than the diameter of the evacuator outlet; therefore, the distal end portion 154 may be inserted inside the evacuator outlet for a friction fit. In another embodiment, the distal end portion 154 may have a slightly larger diameter than the diameter of the evacuator outlet; therefore, the distal end portion 154 may be inserted over the top of the evacuator outlet for a friction fit. In one embodiment, the diameter of the opening of the distal portion 154 for connection to an evacuator may have a diameter of approximately 10 mm.

Referring to FIG. 4, the suction assembly 104 further includes a trigger switch 170 that allows for controlling a suction power of the suction assembly 104. Since the HVE is connected to the handle 122, the adapter 100 may only need to be engaged on an as-needed basis during a procedure, such as a dental procedure. As shown, the trigger switch 170 extends outwardly from the handle 122 and may be electrically connected to a controller that controls an operation of the suction assembly 104. In one embodiment, the trigger switch 170 may be a button that may be depressed to control the suction power of the impeller 134, and hence the adapter 100. More specifically, the more pressure that is applied to the trigger switch 170, the faster the rotational speed of the impeller 134. In another embodiment, the trigger switch 170 is a rotatable, dimmer-type switch that allows an operator to rotate the switch smoothly to increase or decrease the rotational speed of the impeller 134. In another embodiment, the trigger switch 170 may be a simple on/off switch, where the off position maintains the impeller 134 in an idle position, and the on position rotates the impeller at a constant, predetermined rotational speed.

Further, a switch 172 (see FIGS. 3 and 4) allows for turning on and off the suction assembly (i.e., adapter 100) in order to conserve the energy and avoid overheating of the motor 136. In one embodiment, the switch 172 is a three-way switch. In a first position, the switch 172 may turn on the adapter 100 continuously, while in a second position, the switch 172 may turn on the adapter 100 or the impeller 134 as needed by pressing a trigger switch 170. In the third position, the switch 172 may turn off the impeller 134, and hence the adapter 100, completely. In one embodiment, the switch 172 may be a button that may be depressed to turn on and off the adapter 100. In another embodiment, the switch 172 may be a simple flip switch. Other switch configurations, such as a toggle switch, are possible and contemplated. In one embodiment, depressing (or flipping) the switch 172 may cause the switch to illuminate to indicate that the adapter 100 is turned on. In one embodiment, the brightness of the switch when the switch 172 is turned on may increase when the trigger switch 170 is engaged. In another embodiment, the switch 172 may be turned on without any illumination of the switch 172, and the switch 172 may only become illuminated when the trigger switch 170 is engaged.

In one embodiment, as shown in FIG. 4, the switch 172 may be connected to a circuit board 176 of the suction assembly 104. The circuit board 176 may regulate power to a battery 174, and the battery 174, in turn, may provide power to the motor 136. A battery indicator 178 of the suction assembly may also be connected to the circuit board 176. The battery indicator 178 may indicate the current charge state of the battery 174. For example, the battery indicator 178 may have a certain color associated with the charge state of the battery 174. For example, the battery indicator 178 may be green when the battery 174 is fully charged and red when the battery is nearly drained. In one embodiment, an operator may remove the housing 118 and replace the battery 174 when the battery 174 is discharged. In another embodiment, the suction assembly may include a USB port 180 attached to the handle 122, and an operator may connect a charging cable to the USB port 180 to charge the battery 174.

In one embodiment, the motor 136 may be a brushless motor. In such a case, the circuit board 176 may also include an escape board (ESC board) 182. The ESC board 182 is an electronic circuit that controls and regulates the speed of the motor 136. Additionally, when the motor 136 is in operation and engages the impeller 134, the impeller 134 passes cold fluid and vacuum air near or around the motor 136, which may help mitigate overheating of the motor 136. Also, in some embodiments, the battery 174 may be omitted. In such a case, the motor 136 may be connected to a cable that extends outside the adapter 100 and is connected to a power supply means to rotate the motor 136. Also, in such a case, the battery indicator 178 and the USB port 180 may also be omitted.

Referring to FIGS. 1, 2, 5, and 6, the tip structure 116 adapted to be connected to the tube 106 and includes a first portion 190 having a constant diameter and connected to the tube 106. In an embodiment, the first portion 190 may taper outwardly in a direction away from the tube 106. Further, the first portion 190 transitions to a center portion 192 of the tip structure 116. As shown, the center portion 192 tapers inwardly in a direction away from the tube 106 and transitions to a second portion 194. The second portion 194 is a straight portion and has a substantially constant diameter. In one embodiment, a length of the first portion 190 is smaller than a length of the center portion 192. In some embodiments, the length of the first portion 190 is greater than the length of the center portion 192. In one embodiment, the first portion 190 is 10 mm in length and the center portion 192 is 30 mm in length. Additionally, the second portion 194 may have a circular opening 196 for receiving a suction connector, such as a disposable HVE tip. In one embodiment, the circular opening 196 has a diameter of 11 mm. In some embodiments, the second portion 194 may be omitted.

Figure 5:
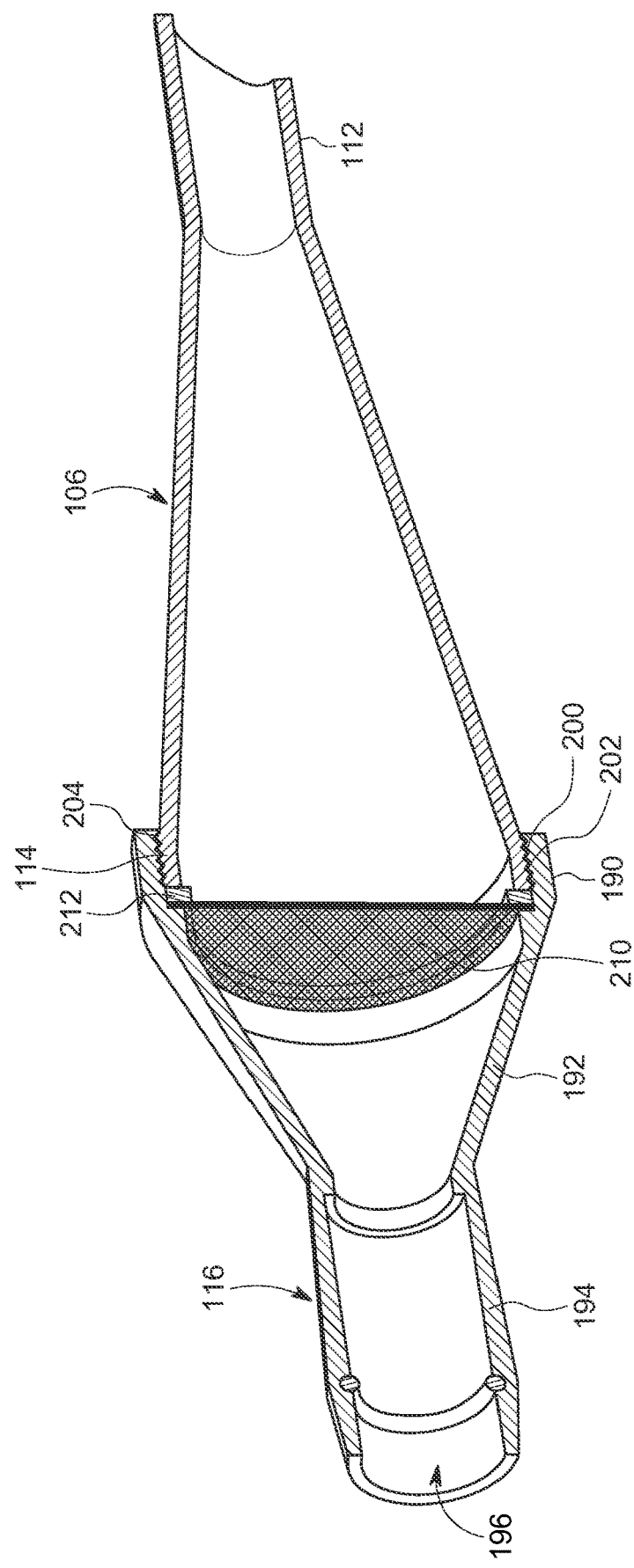
FIG. 5 depicts a sectional view of a tube and a tip structure engaged with the tube, according to an embodiment of the disclosure.
Figure 6:
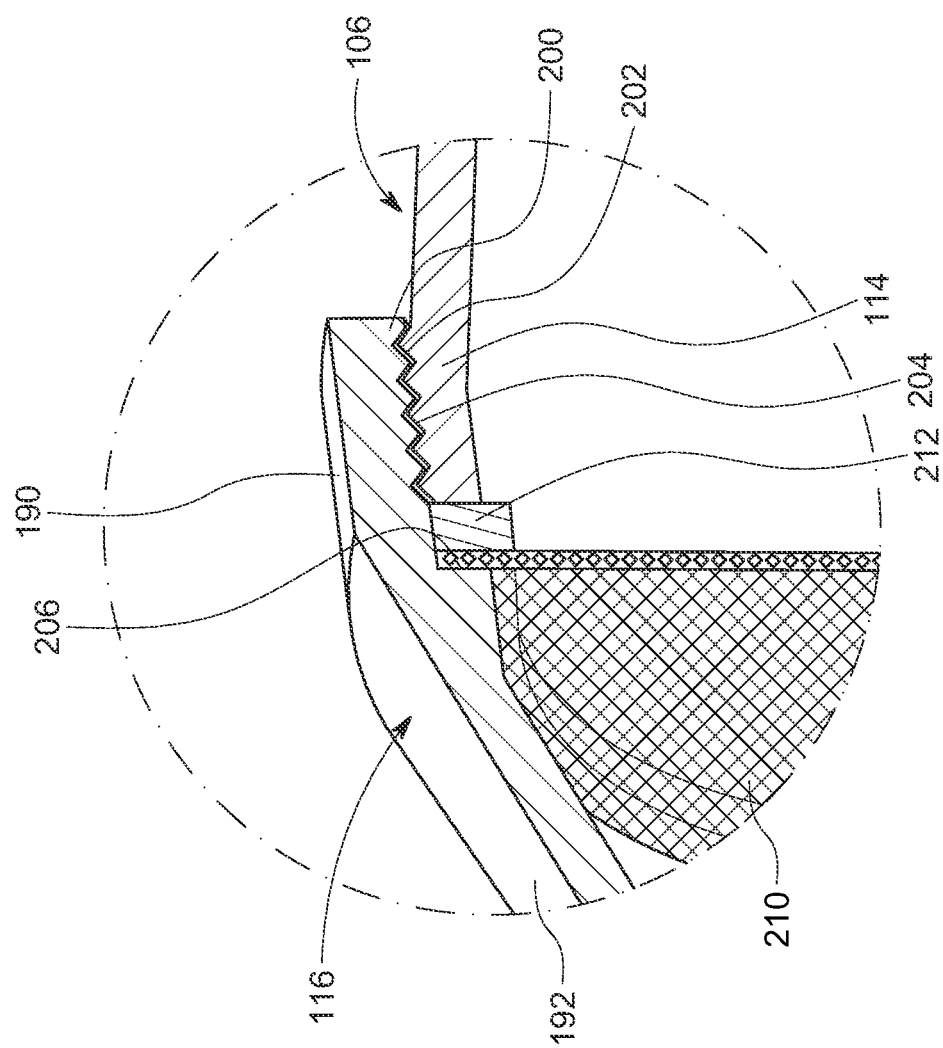
FIG. 6 depicts an enlarged view of a portion of FIG. 5 depicting an interface of the tube and the tip structure, according to an embodiment of the disclosure.

In one embodiment, as shown in FIGS. 5 and 6, the tip structure 116 has a threaded portion 200 having internal threads 202 for threading the tip structure 116 onto outer threads 204 of the tube 106. In another embodiment, the diameter of the first portion 190 of the tip structure 116 is slightly larger than the diameter of the front end section 114 of the tube 106, providing for a friction fit of the tube 106 with the tip structure 116. The threaded portion 200 may include a face 206 or flange extending radially inwardly from a wall of the tip structure 116 to support and abut a mesh 210 arranged at an interface of the tube 106 with the tip structure 116. In the embodiment, the mesh 210 is sandwiched between the face 206 and a seal ring 212 arranged inside the tip structure 116 to prevent a leakage of fluid at the interface of the tip structure 116 and the tube 106. In some embodiments, the face 206 may define an annular depression sized to insert the mesh 210. In one embodiment, the mesh 210 may be friction fit into the depression. The mesh 210 may protect the impeller 134 of the suction assembly 104 from solid objects suctioned into the adapter 100. In one embodiment, the mesh 210 may be removable for cleaning or for replacement with another mesh. In one embodiment, the mesh 210 is made of a thin metal material, such as copper, or alternatively stainless steel mesh or plastic material. In one embodiment, the mesh may have holes sized to capture large particles and debris.

Figure 7:
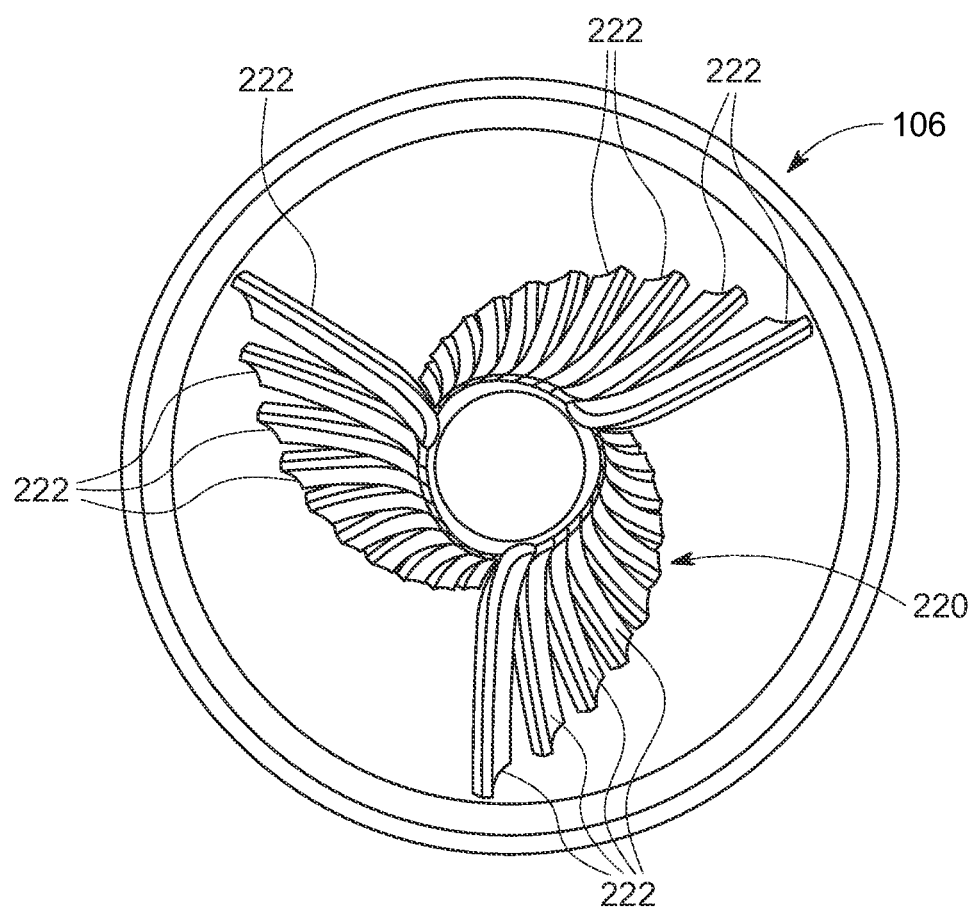
FIG. 7 depicts an enlarged view of a shark fin tube as seen looking down through a front end of the tube, according to an embodiment of the disclosure.
Figure 8:
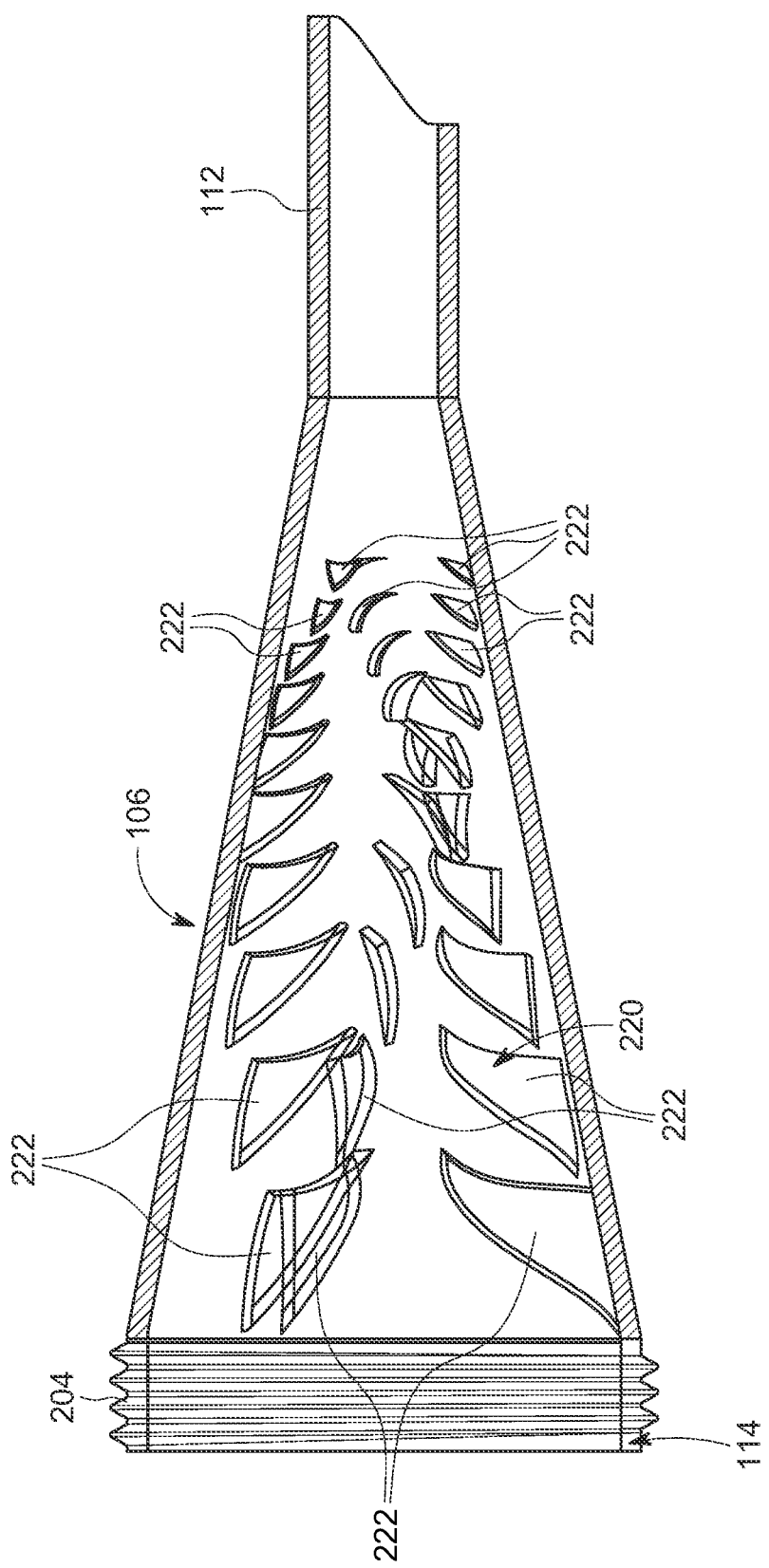
FIG. 8 depicts a side, perspective view of the shark fin tube of FIG. 7 having a plurality of fins arranged inside the tube of the adapter, according to an embodiment of the disclosure.
Figure 9:
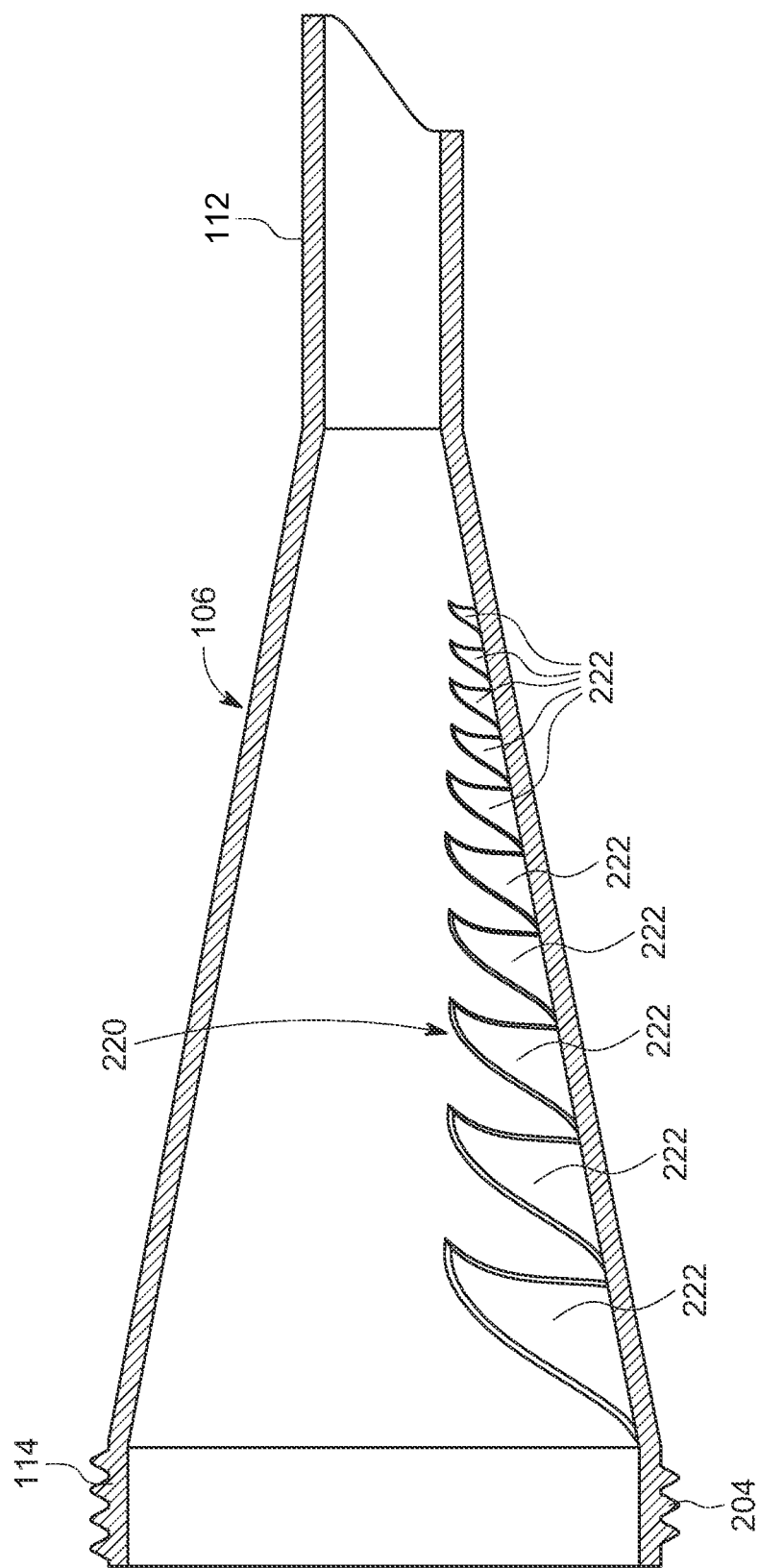
FIG. 9 depicts a side view of the shark fin tube depicting a single row of fins, according to an embodiment of the disclosure.

Referring to FIGS. 7, 8, and 9, the adapter 100 may further include a continuous static vortex impeller mechanism 220 (i.e., impeller mechanism 220) located along the inner wall of the tube 106. The impeller mechanism 220 includes a plurality of fins 222 running along the inner wall of the tube 106. The fins 222 may be shark fin-shaped with sharp blades of certain angles (e.g., an S-shape). The impeller mechanism 220 may create a vortex and disintegrate particles (e.g., blood clots or small objects) to enhance fluid dynamics. The particles entering the tube 106 and passing through the impeller mechanism 220 spin inside the tube 106 due to the orientation of the fins 222 within the tube 106. The vortex pattern causes rotation of the fluid and breaks up the particles. In one embodiment, as the fluid encounters a set of fins 222, the fluid will rotate. In one embodiment, the fluid undergoes one full rotation through the tube 106.

In an embodiment, the plurality of fins 222 are arranged in a plurality of rows, for example, three rows, extending spirally/helically from the front end section 114 of the tube 106 to the rear end section 112 of the tube 106. Further, the fins 222 in each row are arranged spaced apart from each other by a predefined distance. Also, the fins 222 in each row are angularly oriented from adjacent fins by a predefined angle. Accordingly, there are three fins 222 per cross-section of the tube 106, where each cross-section is at a predefined distance from an adjacent cross-section. For example, the tube 106 has cross-sections that are spaced 10 mm apart along the tube 106. In one embodiment, a total of 30 fins 222 are located inside the tube 106. In one embodiment, less than 30 fins 222 may be located inside the tube 106. In one embodiment, the tube 106 is 100 mm in length. The three fins 222 are 120° apart from each other in each cross-section and are arranged at a predefined angular orientation relative to fins 222 arranged in adjacent cross-section. For example, three fins 222 arranged in a second cross-section of the tube 106 are arranged at an angular orientation of 12 degrees from an orientation of the three fins 222 of a first cross-section. In another embodiment, the tube 106 may be 50 mm in length and the fins 222 of a given cross-section are angularly oriented 24 degrees from the fins 222 of adjacent cross-section(s). It may be appreciated that each cross-section may represent the impeller 220 at a moment of time. The rotational flow of the fluid and the sharp edges of the fins 222 may disintegrate particles as the particles pass through the tube 106. In another embodiment, the tube 106 may be designed with fewer fins 222 arranged inside the tube 106 as compared to the previous embodiments. The fins 222 are configured to disintegrate particles such as blood clots and particles as they enter the tube 106, thereby helping to maintain the airflow by preventing from clogging.

Figure 10:
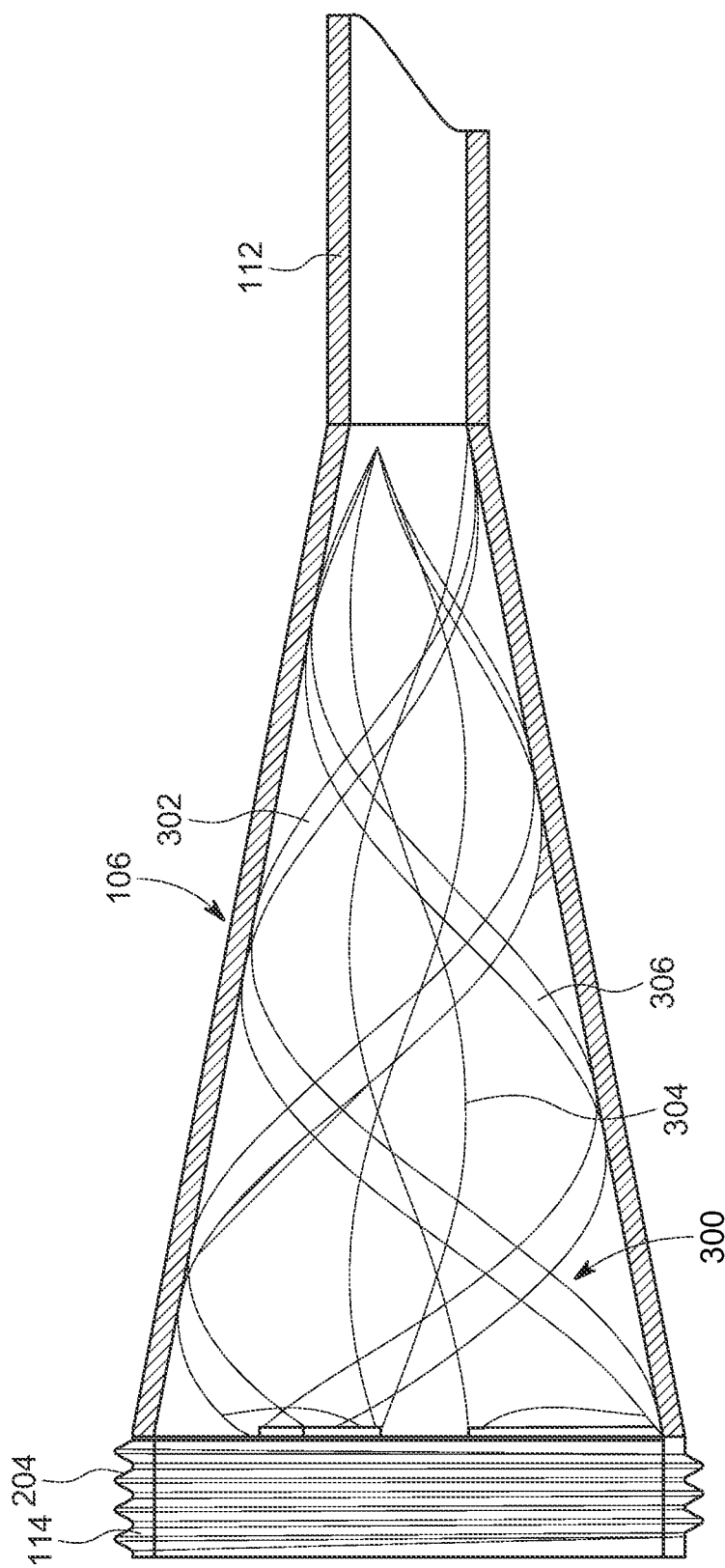
FIG. 10 depicts a side, perspective view of a triple helix tube having a plurality of strands, according to an alternative embodiment of the disclosure.
Figure 11:
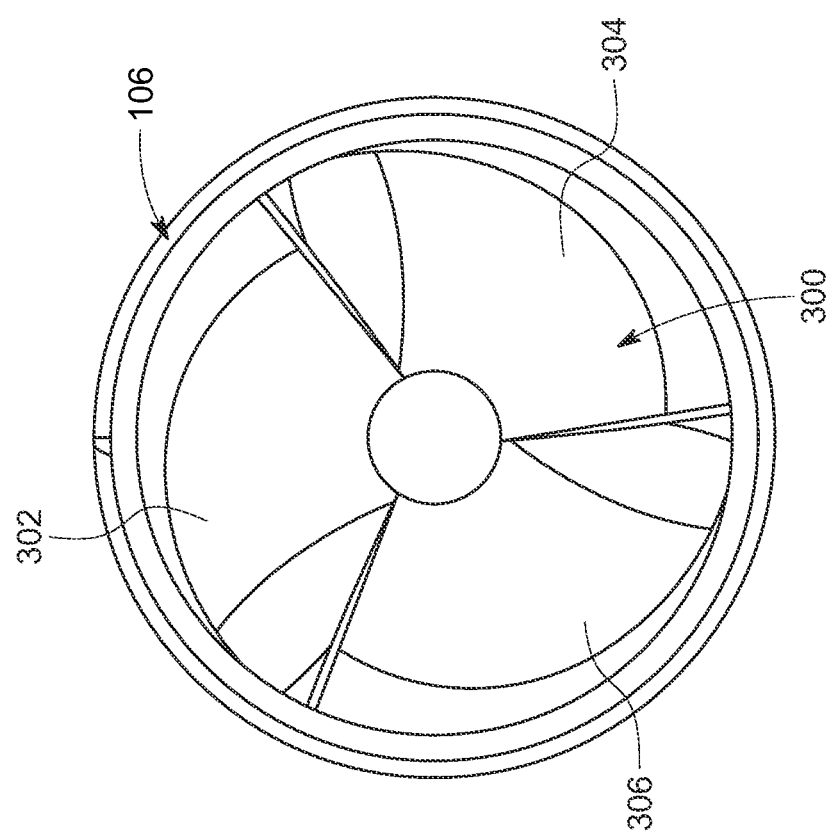
FIG. 11 depicts an enlarged view of the triple helix tube of FIG. 10 as seen looking down through the front end of the tube, according to an embodiment of the disclosure.
Figure 12:
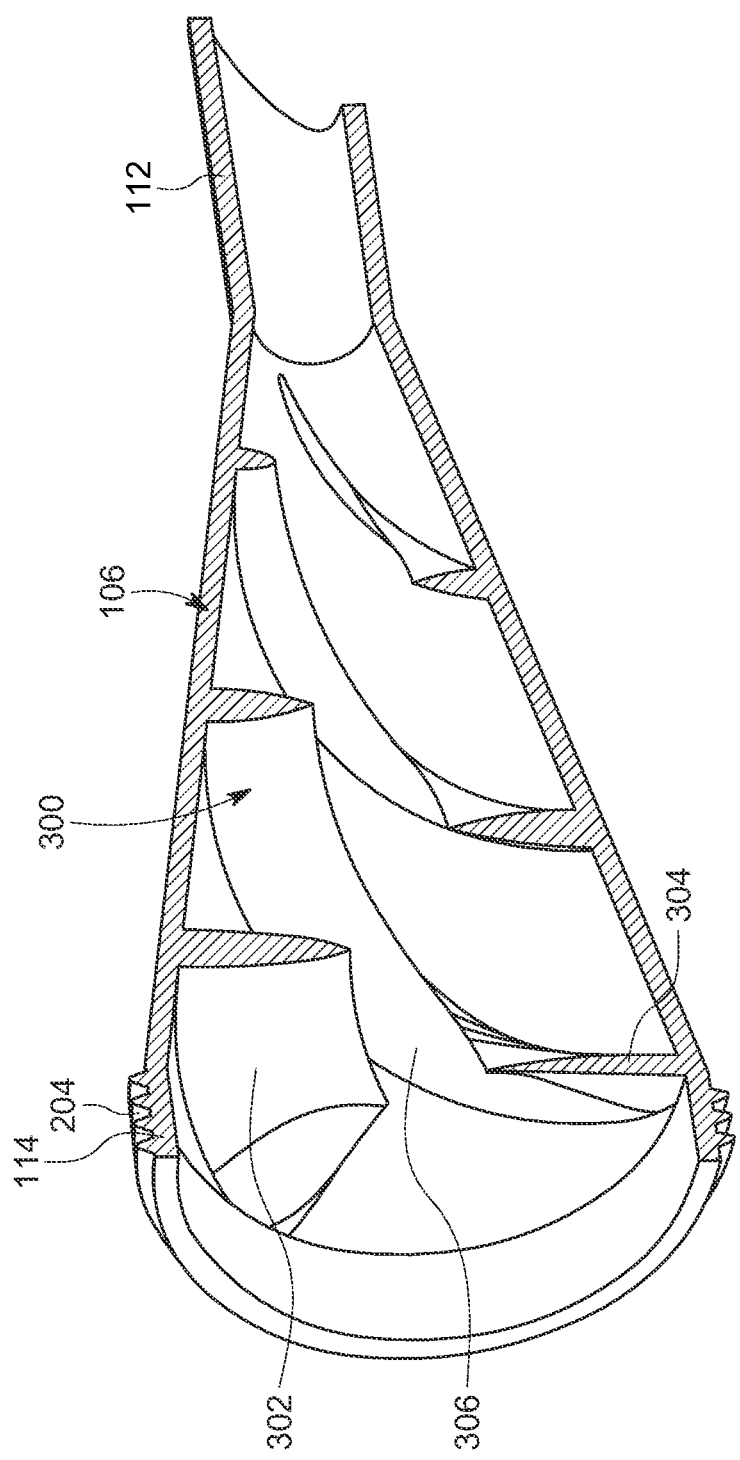
FIG. 12 shows a sectional side view of the triple helix tube depicting the strands of, according to an embodiment of the disclosure.

With respect to FIGS. 10, 11, and 12, an alternative impeller mechanism 300 is shown. The impeller mechanism 300 is a continuous helix vortex impeller mechanism and includes a plurality of strands 302, 304, 306 running along the inner wall of the tube 106. The strands 302, 304, 306 may be curved in such a way along the inside of the tube 106 to create a helical pattern. The strands 302, 304, 306 may have sharp edges. Though each strand 302, 304, 306 runs continuously through the inside wall of the tube 106, at any given cross-section, each of the strands 302, 304, 306 are spaced apart from each other by a fixed, predetermined angle. For example, each of the strands 302, 304, 306 at any given cross-section is 120 degrees apart. Also, the strands 302, 304, 306 rotate by a predefined angle between adjacent cross-sections, wherein the predefined angle depends on a distance between two adjacent cross-sections. For example, the strands 302, 304, 306 of two adjacent cross-sections may be arranged at an angular orientation of 90 degrees when the cross-section are spaced at a predetermined distance from each other. Accordingly, the strands 302, 304, 306 may rotate a full spin (i.e., 360 degrees) as the strands 302, 304, 306 extend from the front end section 114 of the tube 106 to the rear end section 112 of the tube 106. It may be appreciated that each cross-section may represent the impeller mechanism 300 at a moment of time.

The impeller mechanism 300 may create a vortex and disintegrate particles (e.g., blood clots or small objects) to enhance fluid dynamics. The particles entering the tube 106 and passing through the impeller mechanism 300 spin inside tube 106 due to the helical orientation of the strands 302, 304, 306 within the tube 106. The vortex pattern causes rotation of the fluid and breaks up the particles with the sharp edges of the strands 302, 304, 306. In one embodiment, as the fluid encounters the strands 302, 304, 306, the fluid will rotate. In one embodiment, the fluid undergoes one full rotation through the tube 106. The rotational flow of the fluid and the sharp edges of the strands 302, 304, 306 may disintegrate particles as the particles pass through the tube 106. This rotational flow may also increase the velocity of the fluid particles as the fluid particles move through the tube 106. Although the impeller mechanism 220, 300 arranged inside the tube 106 is contemplated, it may be appreciated that the tube 106 is devoid of the impeller mechanism 220, 300. Also, in some embodiments, the tube 106 may be omitted and a standard HVE disposable tube may be directly connected to the suction assembly 104 (e.g., the inlet conduit 140). In another embodiment, the impeller mechanism 220, 300 may also be incorporated in a vacuum cleaner tube to increase the airflow and to prevent objects from clogging the orifice of a dust container. Such a configuration would also save energy, as the impeller mechanism 220, 300 increases suctioning power.

Figure 13:
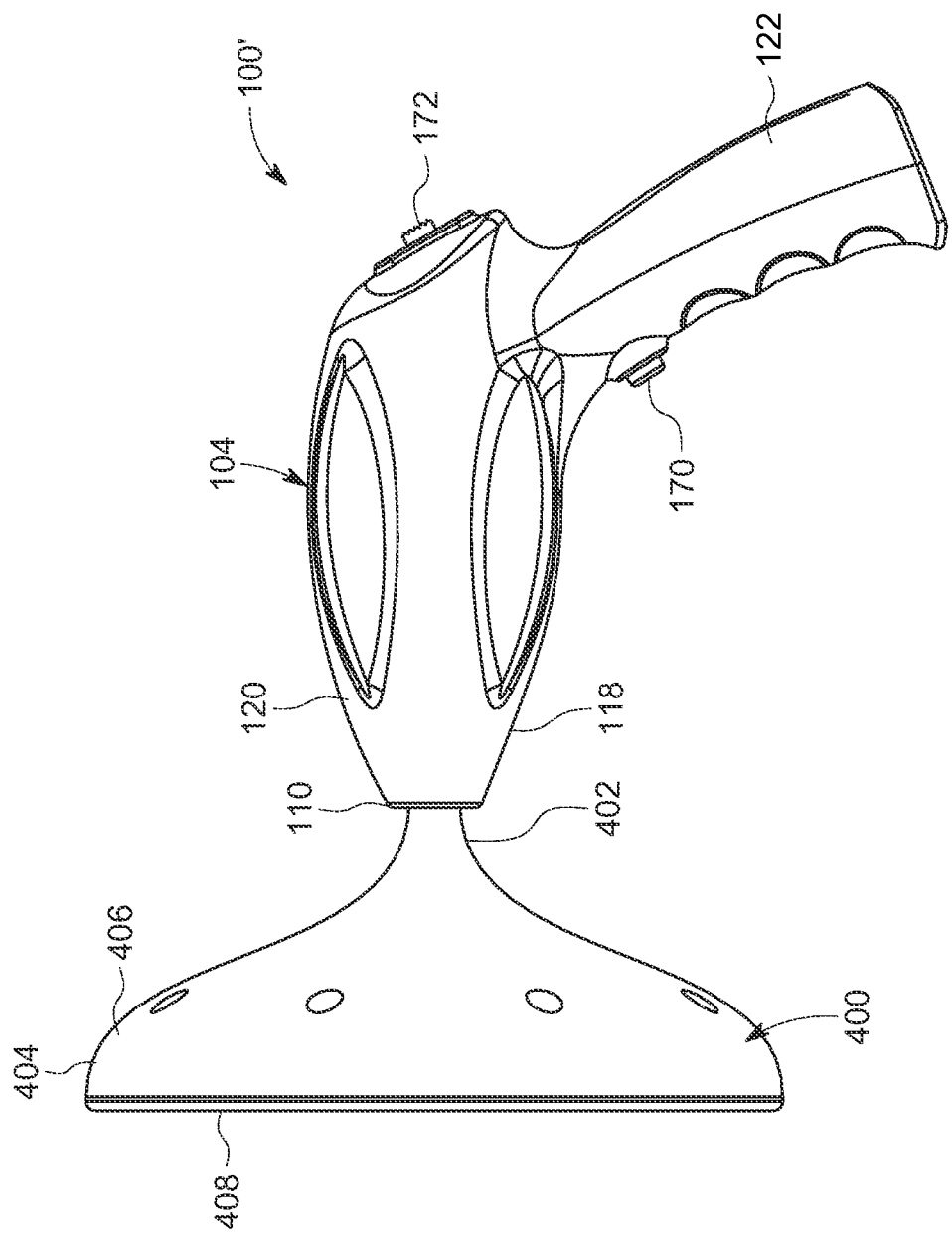
FIG. 13 depicts a side view of an adapter suitable for attachment to an evacuator and having a suction connector, according to an embodiment of the disclosure.
Figure 14:
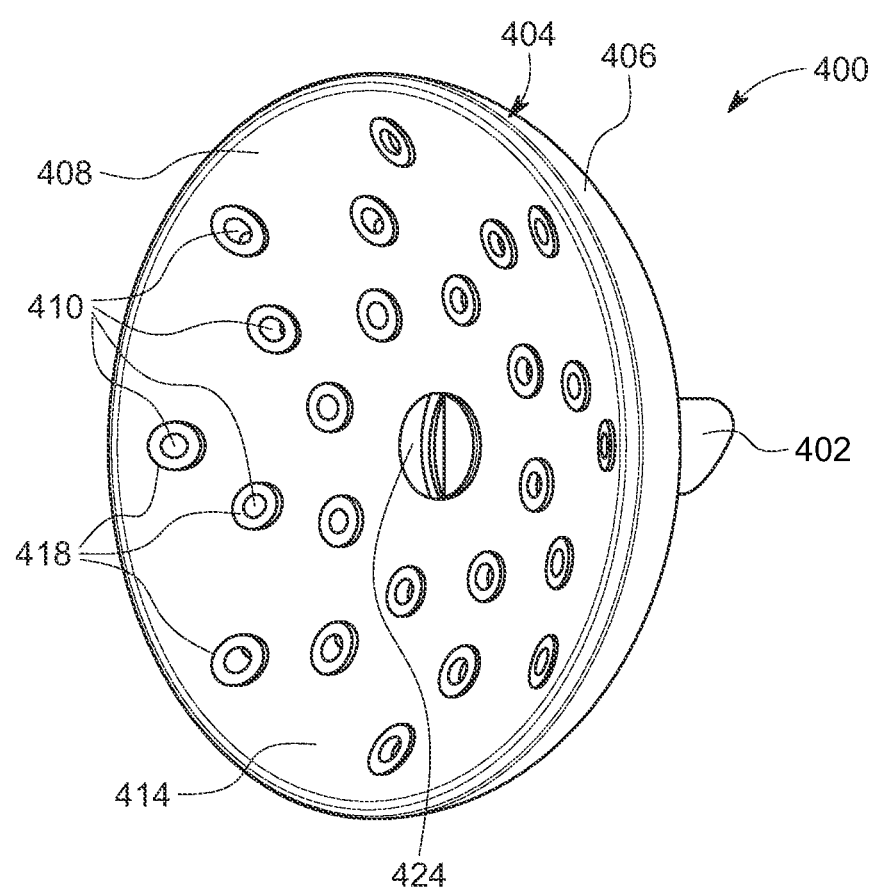
FIG. 14 depicts a front perspective view of the suction connector of FIG. 13, according to an embodiment of the disclosure.
Figure 15:
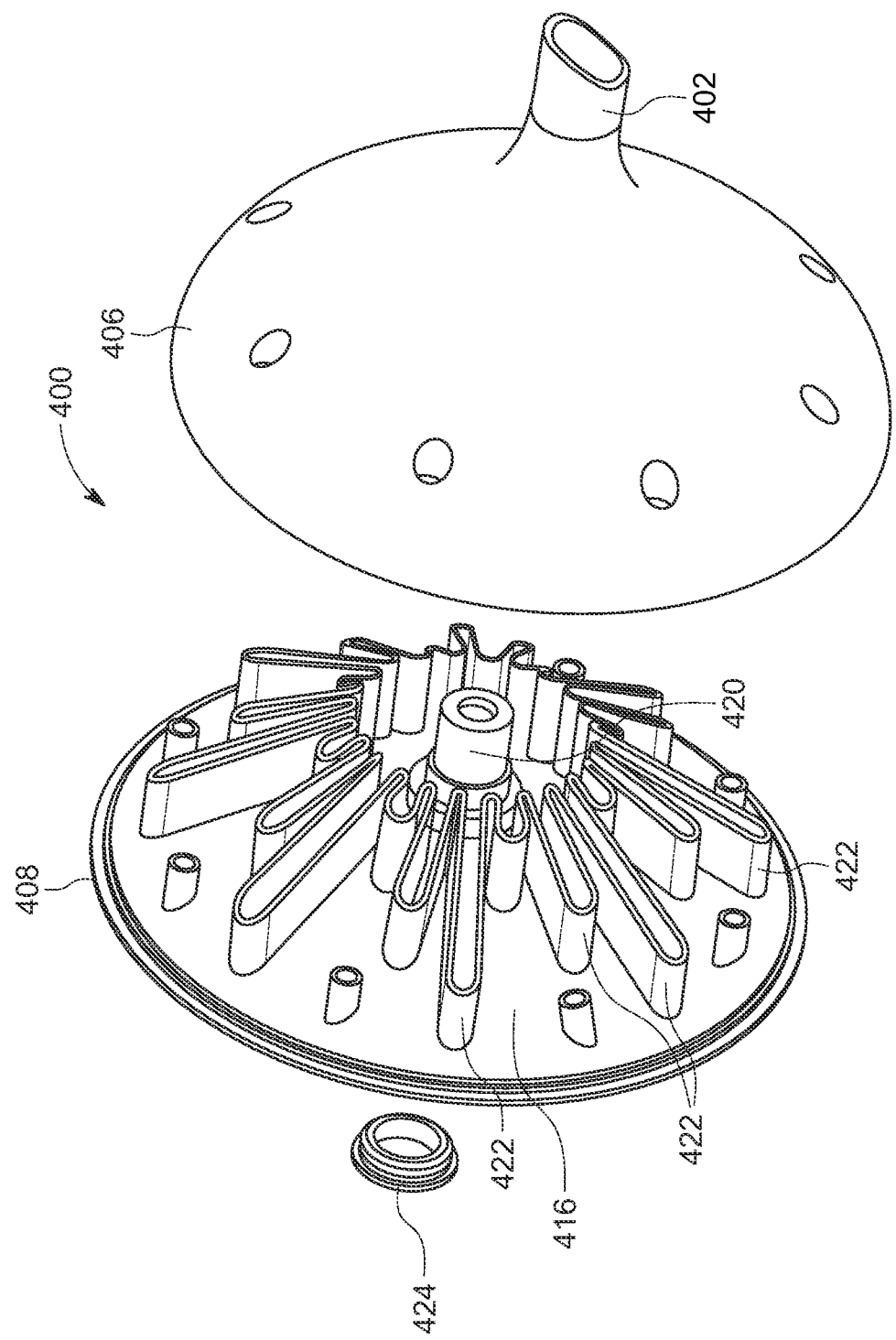
FIG. 15 depicts an exploded view of the suction connector of FIG. 13, according to an embodiment of the disclosure.
Figure 16:
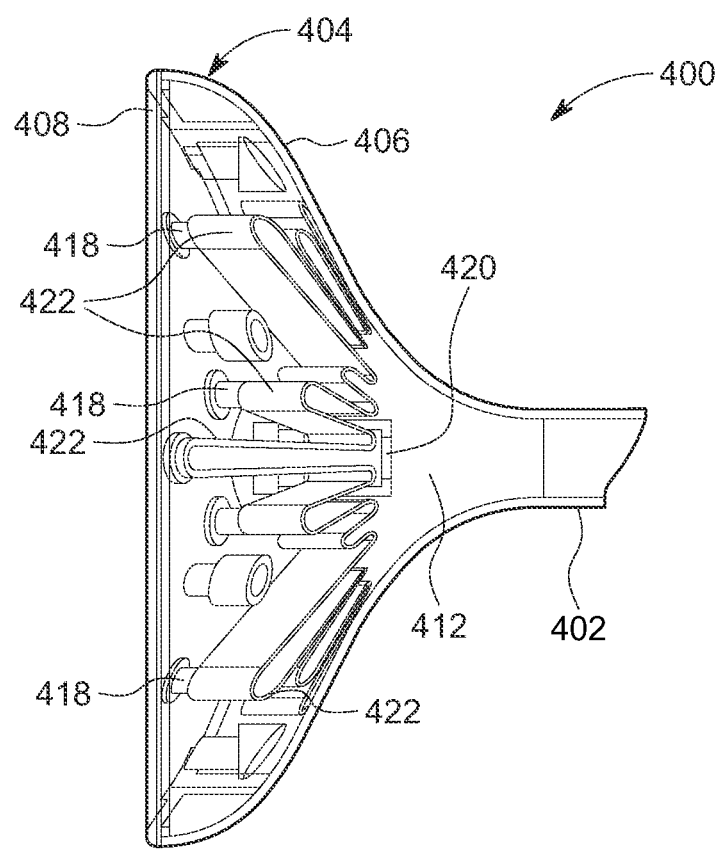
FIG. 16 depicts a rear sectional perspective view of the suction connector of FIG. 13 illustrating a plurality of guide conduits, according to an embodiment of the disclosure.
Figure 17:
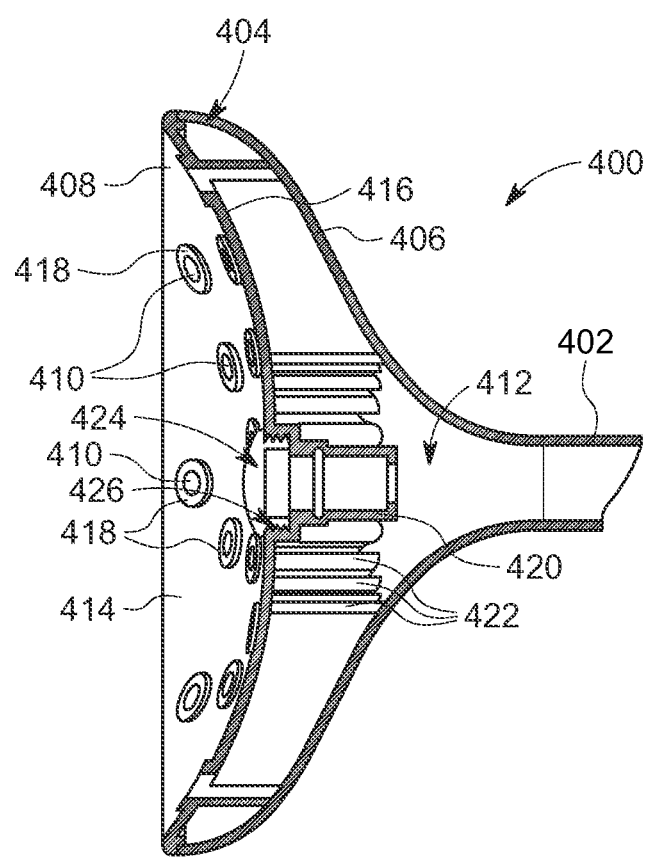
FIG. 17 depicts a front-sectional perspective view of the suction connector of FIG. 13 illustrating a plurality of guide conduits and a plug connected to a central conduit of the suction connector, according to an embodiment of the disclosure.

Referring to FIG. 13, an adapter 100' according to an alternative embodiment is shown. The adapter 100' is similar to the adapter 100 except that the adapter 100' includes a suction connector 400 connected to the suction assembly 104 instead of the tube 106 and the tip structure 116. As shown, the suction connector 400 is adapted to attach to the front end 110 of the suction assembly 104, and may removably attach to the inlet conduit 140 of the suction assembly 104 in a manner similar to the attachment of the tube 106 with the inlet conduit 140. The suction connector 400 is adapted to capture the aerosols and spatters coming outside the mouth, whereas the tube 106 and the tip structure 116 are used to capture fluid and particles inside the mouth. The use of rotary dental and surgical instruments, such as handpieces or ultrasonic scalers and air-water syringes, creates a visible spray that can contain particle droplets of water, saliva, blood, microorganisms, and other debris. The suction connector 400 is configured to capture such droplets, debris, etc.

Referring to FIGS. 13 to 17, the suction connector 400 includes a conduit portion 402 adapted to attach to the inlet conduit 140 and a collector portion 404 for collecting the fluids coming from the mouth and extending outwardly and away from the conduit portion 402. In an embodiment, the collector portion 404 includes a funnel portion 406 attached to the conduit portion 402 and a cover portion 408 attached to the funnel portion 406 and defining a plurality of openings 410 to receive and collect the aerosol from the mouth. In an embodiment, the funnel portion 406 is integrally formed with the conduit portion 402 and may include a substantially frustoconical shape. In an embodiment, the collector portion 404 may include a shape of a shower pad. In an embodiment, the funnel portion 406 may include a substantially hemispherical shape. The conduit portion 402 is arranged substantially centrally to the funnel portion 406 and facilitates a passage of the aerosol collected by the collector portion 404 to the inlet conduit 140. Further, as shown, the cover portion 408 may include a saucer pan shape and attached to the funnel portion 406, defining a cavity 412 therebetween. In one embodiment, the cover portion 408 may be in a threaded engagement with the funnel portion 406. Alternatively, the cover portion 408 may be friction or press fitted with the funnel portion 406. In some embodiments, the cover portion 408 includes a concave shape having a front concave surface 414 and defining the plurality of openings 410 extending from the front surface 414 to a rear surface 416 arranged facing the funnel portion 406. In one embodiment, each opening 410 is defining a funnel or saucer-like component 418 with the opening 410 arranged on the front surface 414. In an embodiment, each opening 410 has a diameter of 5 mm. The openings 410 facilitate an entry or a capture of the aerosol generated from the dental procedures and allows a flow of the aerosol—to the conduit portion 402 via the cavity 412. In an embodiment, the cover portion 408 includes a central conduit 420 extending from the front surface 414 to the rear surface 416 and extending rearwardly of the rear surface 416.

Additionally, or optionally, the cover portion 408 includes a plurality of guide conduits 422 extending inside the cavity 412 and along the rear surface 416 of the cover portion 408 and in communications with the plurality of openings 410 to enable a flow of the aerosol entering the plurality of openings 410 toward the cavity 412 to guide the flow of the aerosol to the conduit portion 402. Further, in an embodiment, the cover portion 408 may include a plug 424 adapted to removably connect to the central conduit 420 to close an inlet port 426 (shown in FIG. 17) of the central conduit 420 defined at a face or the front surface 414 of the cover portion 408. In one embodiment, the inlet port 426 of the central conduit 420 has a diameter of about 10 mm to press fit a disposable HVE tip to enable a suction effect inside the mouth to capture the fluid. In an embodiment, the openings 410 may be oriented in various directions to capture the fluid from all the directions.

A dental procedure may require an LVE and an HVE at the same time, or perhaps, two HVEs at the same time. Using two HVEs at the same time may reduce the suction power (e.g., 30-50% decrease in suction power). Connecting one of the HVEs to the adapter 100, 100' provides increased power. Additionally, detachment of the parts allows a user to clean the inside of each part easily. The outside of the adapter 100, 100' may be wiped with disinfectant. Inside each part of the adapter, a user may apply a diluted bleach solution, enzymatic solution, or the like.

It is contemplated that various combinations and/or subcombinations of the specific features and aspects of the above embodiments may be made and still fall within the scope of the invention. Accordingly, it should be understood that various features and aspects of the disclosed embodiments may be combined with or substituted for one another in order to form varying modes of the disclosed invention. Further, it is intended that the scope of the present invention is herein disclosed by way of examples and should not be limited by the particular disclosed embodiments described above.

What is claimed is:

1. An adapter for an evacuator, comprising:
a suction assembly adapted to be coupled with the evacuator, wherein the suction assembly comprising:
a housing;
an impeller assembly arranged inside the housing, wherein the impeller assembly includes an impeller, a motor driving the impeller, and an impeller housing, wherein the impeller assembly is configured to provide a suction;
an inlet conduit to facilitate a flow of fluid to the impeller; and
an outlet conduit arranged inside the housing and adapted to be coupled to the evacuator,
wherein the outlet conduit is in fluid communication with the impeller and facilitates the flow of the fluid from the suction assembly to the evacuator,
wherein a first end of the outlet conduit is attached to the impeller assembly and a second end of the outlet conduit is configured to receive a connection of the evacuator,
wherein an opening of the first end of the outlet conduit which is attached to the impeller assembly is larger than an opening of the second end of the outlet conduit which is configured to receive the connection of the evacuator, and
wherein the adapter is configured to restrict airflow to a predetermined threshold based on a configuration of each of the outlet conduit and the impeller assembly.

2. The adapter of claim 1 further comprising a tube removably coupled to the inlet conduit and arranged outside the housing, wherein the tube is a venturi tube and tapers outwardly from the inlet conduit in a direction away from the inlet conduit.

3. The adapter of claim 2 further comprising a tip structure coupled to the tube configured to enable suctioning of fluid from inside of a mouth of a patient.

4. The adapter of claim 3 further comprising a mesh arranged at an interface of the tip structure and the tube to protect the impeller from solid objects.

5. The adapter of claim 2 further comprising an impeller mechanism arranged along an inner wall of the tube to create a vortex inside the tube and disintegrate particles present flowing through the tube.

6. The adapter of claim 5, wherein the impeller mechanism comprises a plurality of fins arranged in a plurality of rows inside the tube, wherein each row extends spirally from a first end section of the tube to a second end section of the tube.

7. The adapter of claim 6, wherein the fins arranged at a cross-section of the tube are arranged at a predefined angular orientation from the fins arranged at an adjacent cross-section.

8. The adapter of claim 6, wherein each fin includes a shark fin shape.

9. The adapter of claim 5, wherein the impeller mechanism comprises a plurality of helical strands extending from a front end section of the tube to a rear-end section of the tube.

10. The adapter of claim 9, wherein the strands are arranged at a fixed predetermined angle relative to each other throughout the extension of the strands inside the tube.

11. The adapter of claim 9, wherein each of the plurality of strands includes a sharp edge to facilitate a breaking of the particles present inside the fluid.

12. The adapter of claim 1, further comprising a suction connector adapted to engage with the inlet conduit to facilitate a capture of aerosols coming outside a mouth of a patient, wherein the suction connector includes:
- a conduit portion adapted to engage with the inlet conduit, and
- a collector portion to collect the aerosols and extending outwardly and away from the conduit portion.

13. The adapter of claim 12, wherein the collector portion comprises:
- a funnel portion engaged with the conduit portion; and
- a cover portion adapted to removably engage with the funnel portion and defining a cavity therebetween, wherein the cover portion defines a plurality of openings to capture the aerosols and spatters coming outside the mouth of the patient.

14. The adapter of claim 13, wherein the cover portion comprises a plurality of guide conduits extending inside the cavity and along a rear surface of the cover portion, and wherein the plurality of guide conduits is in fluid communication with the plurality of openings to enable the flow of the fluid entering the plurality of openings to the conduit portion.

15. The adapter of claim 13, wherein the cover portion comprises a concave shape having a front concave surface, and wherein the plurality of openings is defined at the front concave surface.

16. The adapter of claim 12, wherein the collector portion comprises a shape of a substantially circular shower pad.

17. The adapter of claim 1, wherein the suction assembly further comprises a trigger switch to control a suction power of the adapter.

18. The adapter of claim 17, wherein the trigger switch controls a rotational speed of the impeller to control the suction power of the adapter.

19. The adapter of claim 1, wherein the housing comprises a hand-gun shape having a barrel portion and a handle, wherein the inlet conduit is arranged inside the barrel portion and the outlet conduit extends inside the handle, wherein the outlet conduit tapers inwardly from the impeller in a direction away from the impeller along a length of the handle, and wherein the handle extends downwardly from the barrel portion and is arranged at an angle greater than or equal to 90 degrees relative to the barrel portion.

20. The adapter of claim 1, wherein the predetermined threshold of airflow is 4.5 Standard Cubic Feet per Minute (SCFM) or less.

* * * * *